(12) United States Patent
Kostrzewski

(10) Patent No.: US 8,070,038 B2
(45) Date of Patent: Dec. 6, 2011

(54) SURGICAL INSTRUMENT WITH PIVOTABLE JAW MEMBER

(75) Inventor: Stanislaw Kostrzewski, Newtown, CT (US)

(73) Assignee: Tyco Healthcare Group, LP, New Haven, CT (US)

( * ) Notice: Subject to any disclaimer, the term of this patent is extended or adjusted under 35 U.S.C. 154(b) by 320 days.

(21) Appl. No.: 12/249,182

(22) Filed: Oct. 10, 2008

(65) Prior Publication Data

US 2010/0089973 A1 Apr. 15, 2010

(51) Int. Cl.
*A61B 17/068* (2006.01)

(52) U.S. Cl. .................. 227/180.1; 227/175.1; 227/19; 606/219

(58) Field of Classification Search .... 227/175.1–182.1, 227/19
See application file for complete search history.

(56) References Cited

U.S. PATENT DOCUMENTS

| | | | |
|---|---|---|---|
| 4,354,628 A | 10/1982 | Green | |
| 4,383,634 A | 5/1983 | Green | |
| 4,470,533 A | 9/1984 | Schuler | |
| 4,506,670 A | 3/1985 | Crossley | |
| 4,506,671 A | 3/1985 | Green | |
| 4,508,253 A | 4/1985 | Green | |
| 4,522,327 A | 6/1985 | Korthoff et al. | |
| 4,530,453 A | 7/1985 | Green | |
| 4,566,620 A | 1/1986 | Green et al. | |
| 4,568,009 A | 2/1986 | Green | |
| 4,573,622 A | 3/1986 | Green et al. | |
| 4,580,712 A | 4/1986 | Green | |
| 4,632,290 A | 12/1986 | Green et al. | |
| 4,665,916 A | 5/1987 | Green | |
| 4,714,187 A | 12/1987 | Green | |
| 4,715,520 A | 12/1987 | Roehr, Jr. et al. | |
| 4,728,020 A | 3/1988 | Green et al. | |
| 4,767,044 A * | 8/1988 | Green | 227/19 |
| 4,802,614 A | 2/1989 | Green et al. | |
| 4,819,853 A | 4/1989 | Green | |
| 4,848,637 A | 7/1989 | Pruitt | |
| 4,869,414 A | 9/1989 | Green et al. | |
| 4,881,544 A | 11/1989 | Green et al. | |
| 4,881,545 A | 11/1989 | Isaacs et al. | |
| 4,915,100 A | 4/1990 | Green | |
| 4,930,503 A | 6/1990 | Pruitt | |
| 4,941,623 A | 7/1990 | Pruitt | |
| 5,071,052 A | 12/1991 | Rodak et al. | |
| 5,100,042 A | 3/1992 | Gravener et al. | |
| 5,116,349 A | 5/1992 | Aranyi | |
| 5,190,203 A | 3/1993 | Rodak | |
| 5,312,023 A * | 5/1994 | Green et al. | 227/175.1 |
| 5,344,060 A | 9/1994 | Gravener et al. | |
| 5,368,599 A | 11/1994 | Hirsch et al. | |
| 5,405,073 A * | 4/1995 | Porter | 227/175.1 |
| 5,413,267 A | 5/1995 | Solyntjes et al. | |
| 5,439,155 A | 8/1995 | Viola | |
| 5,452,836 A * | 9/1995 | Huitema et al. | 227/176.1 |
| 5,462,215 A | 10/1995 | Viola et al. | |
| 5,464,144 A | 11/1995 | Guy et al. | |

(Continued)

*Primary Examiner* — Lindsay Low

(57) ABSTRACT

A surgical instrument for surgically joining tissue is disclosed. The surgical instrument includes a handle assembly, an elongated portion extending distally from the handle assembly and defining a longitudinal axis, and an end effector disposed adjacent a distal portion of the elongated portion. The end effector includes a first jaw member and a second jaw member. The first jaw member defines a first axis, which is transverse to the longitudinal axis. The first jaw member is pivotable about the first axis. At least one of the first jaw member and the second jaw member is movable with respect to the other between a spaced-apart and an approximated position.

14 Claims, 5 Drawing Sheets

U.S. PATENT DOCUMENTS

| | | | | |
|---|---|---|---|---|
| 5,465,894 A | * | 11/1995 | Clark et al. | 227/175.1 |
| 5,470,006 A | | 11/1995 | Rodak | |
| 5,470,008 A | | 11/1995 | Rodak | |
| 5,470,009 A | | 11/1995 | Rodak | |
| 5,497,934 A | | 3/1996 | Brady et al. | |
| 5,503,320 A | | 4/1996 | Webster et al. | |
| 5,509,596 A | | 4/1996 | Green et al. | |
| 5,542,594 A | | 8/1996 | McKean et al. | |
| 5,547,117 A | * | 8/1996 | Hamblin et al. | 227/175.2 |
| 5,558,266 A | | 9/1996 | Green et al. | |
| 5,579,978 A | | 12/1996 | Green et al. | |
| 5,603,443 A | * | 2/1997 | Clark et al. | 227/178.1 |
| 5,615,820 A | | 4/1997 | Viola | |
| 5,706,997 A | | 1/1998 | Green et al. | |
| 5,706,998 A | | 1/1998 | Plyley et al. | |
| 5,732,871 A | | 3/1998 | Clark et al. | |
| 5,735,445 A | | 4/1998 | Vidal et al. | |
| 5,810,240 A | | 9/1998 | Robertson | |
| 5,833,695 A | * | 11/1998 | Yoon | 606/139 |
| 5,878,937 A | | 3/1999 | Green et al. | |
| 5,893,506 A | | 4/1999 | Powell | |
| 5,894,979 A | | 4/1999 | Powell | |
| 5,897,562 A | | 4/1999 | Bolanos et al. | |
| 5,964,394 A | | 10/1999 | Robertson | |
| 6,045,560 A | | 4/2000 | McKean et al. | |
| 6,817,508 B1 | | 11/2004 | Racenet et al. | |
| 7,070,083 B2 | | 7/2006 | Jankowski | |
| 7,237,708 B1 | | 7/2007 | Guy et al. | |
| 2004/0164123 A1 | | 8/2004 | Racenet | |
| 2007/0233161 A1 | | 10/2007 | Weller et al. | |
| 2008/0041918 A1 | | 2/2008 | Holsten | |

* cited by examiner

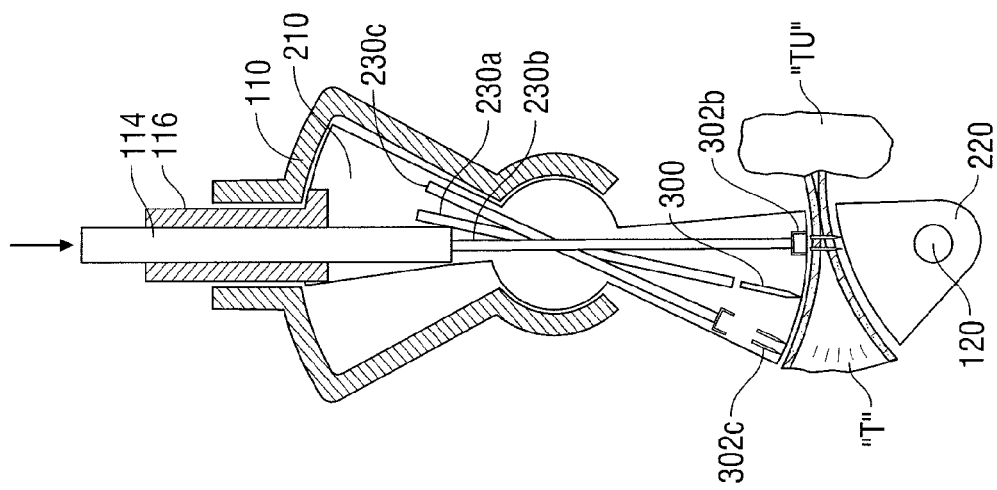
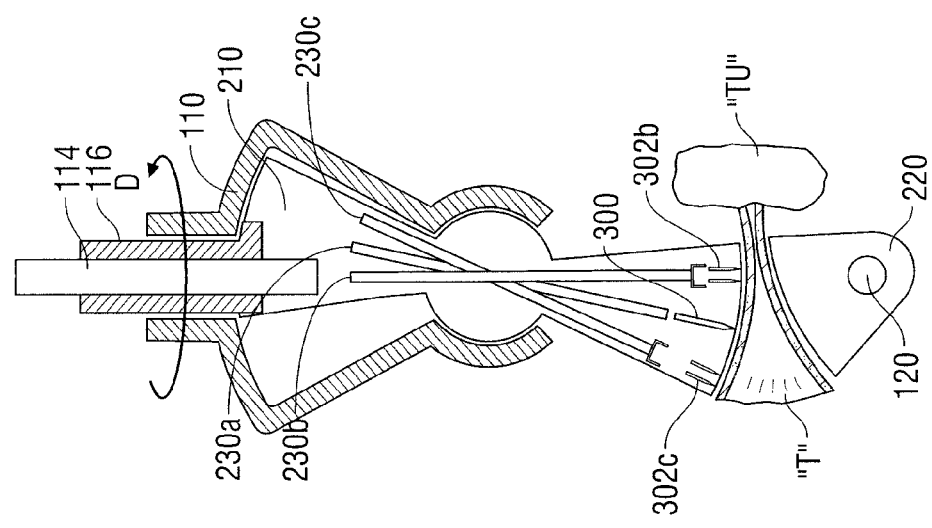
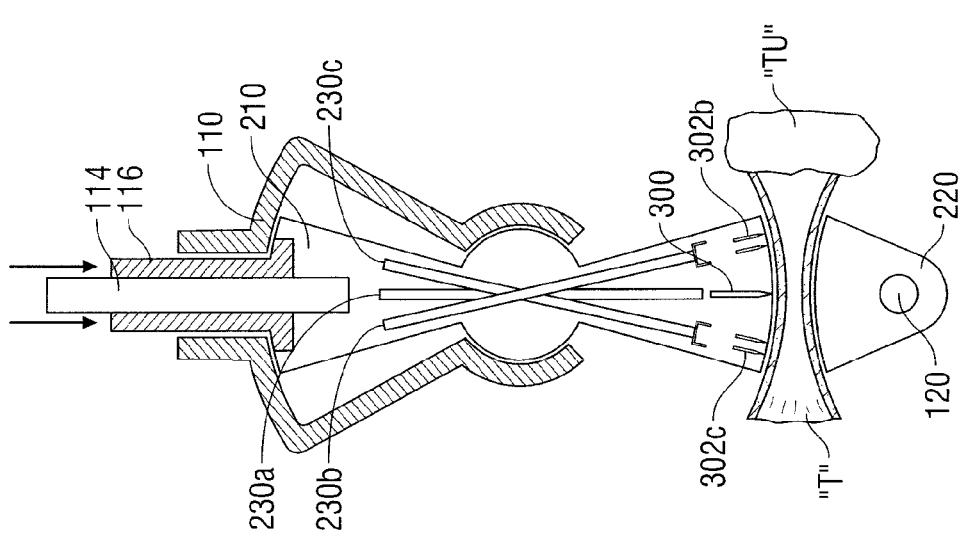

SURGICAL INSTRUMENT WITH PIVOTABLE JAW MEMBER

BACKGROUND

1. Technical Field

The present disclosure relates generally to instruments for surgically joining tissue. More specifically, the present disclosure relates to a surgical instrument having a pivotable jaw member.

2. Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples (e.g., a row of staples) in tissue. Additionally, the surgeon may use the same instrument or a separate instrument emplace more staples (e.g., another row) and/or to cut the tissue adjacent or between the row(s) of staples.

Other examples of a surgical instrument of the present disclosure include electrosurgical (e.g., monopolar and bipolar) forceps. Electrosurgical forceps utilize both mechanical clamping action and electrical energy to affect hemostasis by heating the tissue and blood vessels to coagulate, cauterize and/or seal tissue.

SUMMARY

The present disclosure relates to a surgical instrument for surgically joining tissue. The surgical instrument includes a handle assembly, an elongated portion and an end effector. The elongated portion extends distally from the handle assembly and defines a longitudinal axis. The end effector is disposed adjacent a distal portion of the elongated portion and includes a first jaw member (e.g., cartridge assembly) and a second jaw member (e.g., anvil assembly). The first jaw member defines a first axis extending along the first jaw member, which is transverse to the longitudinal axis of the elongated portion. The first jaw member is pivotable about the first axis. At least one of the first jaw member and the second jaw member is movable with respect to the other between a spaced-apart position and an approximated position.

In a disclosed embodiment, the second jaw member defines a second axis extending along the second jaw member, which is parallel to the first axis; the second jaw member is pivotable about the second axis. Here, the second jaw member may be configured to pivot about the second axis in response to pivoting of the first jaw member about the first axis. In a further embodiment, the second jaw member is configured to pivot in an opposite direction as the first jaw member.

In an embodiment of the present disclosure, the cartridge assembly includes two rows of staples therein and each row of staples is individually actuatable. In this embodiment, the cartridge assembly may include a knife disposed at least partially therein and that each of the knife and the two rows of staples is individually actuatable. Here, the cartridge assembly may include three angularly offset pushers disposed therein; each of the pushers is independently movable with respect to each other.

In a disclosed embodiment, the surgical instrument includes a firing rod disposed in mechanical cooperation with the handle assembly. The firing rod is configured to individually engage at least two angularly offset pushers disposed at least partially within the first jaw member.

The present disclosure also relates to a method of surgically joining tissue. The method includes the step of providing a surgical stapling instrument including a handle assembly, an elongated portion and an end effector. The elongated portion extends distally from the handle assembly and defines a longitudinal axis. The end effector is disposed adjacent a distal portion of the elongated portion and includes a first jaw member, which defines a first axis, and a second jaw member, which defines a second axis. The method also includes the steps of positioning the end effector adjacent tissue, moving at least one of the first jaw member and the second jaw member towards the other from a spaced-apart position to an approximated position to engage tissue therebetween, pivoting the first jaw member about the first axis, and pivoting the second jaw member about the second axis.

In a disclosed embodiment, the method includes the step of firing a first row of staples from the first jaw member towards the second jaw member. Here, an additional step may include firing a second row of staples from the first jaw member towards the second jaw member, where the second row of staples is fired independently of the first row of staples. The step of pivoting the first jaw member and the second jaw member may be between the step of firing the first row of staples and the step of firing the second row of staples.

In an embodiment of the disclosed method, the longitudinal axis is transverse to the first axis. In a disclosed method, the first axis is parallel to the second axis.

The present disclosure also relates to a loading unit configured for releasable engagement with a surgical instrument. The loading unit includes a cartridge assembly configured for releasable engagement with a cartridge housing of the surgical instrument, and an anvil assembly configured for releasable engagement with an anvil housing of the surgical instrument. The cartridge assembly is pivotable with respect to the cartridge housing when the cartridge assembly is engaged with the cartridge housing.

In a disclosed embodiment of the loading unit, the anvil assembly is pivotable with respect to the anvil housing when the anvil assembly is engaged with the anvil housing. Here, the cartridge assembly and the anvil assembly may be independently pivotable of each other.

In an embodiment of the present disclosure, the cartridge assembly and the anvil assembly are releasably secured to each other via a breakable connector. In another embodiment, the anvil assembly includes a bore disposed at least partially therethrough and the bore is configured to mechanically engage a post of the surgical instrument.

In a further aspect of the present disclosure, a surgical instrument for surgically joining tissue comprises a handle assembly; an elongated portion extending distally from the handle assembly and defining a longitudinal axis; and an end effector disposed adjacent a distal portion of the elongated portion. The end effector includes a first jaw member defining a first axis extending along the first jaw member, the first axis extending generally in the same direction as the longitudinal axis of the elongated portion, the first jaw member being pivotable about the first axis. A second jaw member in included. At least one of the first jaw member and the second jaw member is movable with respect to the other between a spaced-apart position and an approximated position.

The second jaw member may define a second axis extending along the second jaw member, the second axis being parallel to the first axis. The second jaw member is pivotable about the second axis.

The second jaw member is configured to pivot about the second axis in response to pivoting of the first jaw member about the first axis, in certain embodiments. The second jaw member can be configured to pivot in an opposite direction as the first jaw member.

The first jaw member may include a cartridge assembly and the second jaw member may include an anvil assembly. In certain embodiments, the cartridge assembly includes two rows of staples therein and each row of staples can be individually actuatable. The cartridge assembly can include a knife disposed at least partially therein and each of the knife and the two rows of staples can be individually actuatable.

The cartridge assembly, in certain embodiments, includes three angularly offset pushers disposed therein and wherein each of the three pushers is independently moveable with respect to each other. The surgical instrument desirably includes a firing rod disposed in mechanical cooperation with the handle assembly, the firing rod being configured to individually engage at least two angularly offset pushers disposed at least partially within the first jaw member.

In another aspect of the present disclosure, a surgical instrument for surgically joining tissue comprises a handle assembly; an elongated portion extending distally from the handle assembly and defining a longitudinal axis; and an end effector disposed adjacent a distal portion of the elongated portion. The end effector includes a first jaw member defining a first axis extending along the first jaw member, the first jaw member being pivotable about the first axis and including a cartridge assembly, the cartridge assembly having a first row of surgical fasteners of a first type and a second row of surgical fasteners of a second type; and a second jaw member including an anvil assembly. At least one of the first jaw member and the second jaw member is movable with respect to the other between a spaced-apart position and an approximated position.

The second jaw member may define a second axis extending along the second jaw member, the second axis being parallel to the first axis, and the second jaw member may be pivotable about the second axis.

The first type can be selected from the group consisting of: a material, a size, staples, and two-part fasteners. The second type is selected from the group consisting of: a metal material, a polymeric material, a staple leg length, and two-part fasteners. The first type is different from the second type.

In certain embodiments, the cartridge assembly includes two rows of staples therein and each row of staples can be individually actuatable. The cartridge assembly can include a knife disposed at least partially therein and each of the knife and the two rows of staples can be individually actuatable.

BRIEF DESCRIPTION OF FIGURES

Various embodiments of the presently disclosed surgical instrument are disclosed herein with reference to the drawings, wherein:

FIGS. 5A-5E are transverse cross-sectional views of the loading unit of FIGS. 2-4 interacting with a portion of the surgical instrument of FIG. 1, shown at various stages of operation.

DETAILED DESCRIPTION

Figure 1:
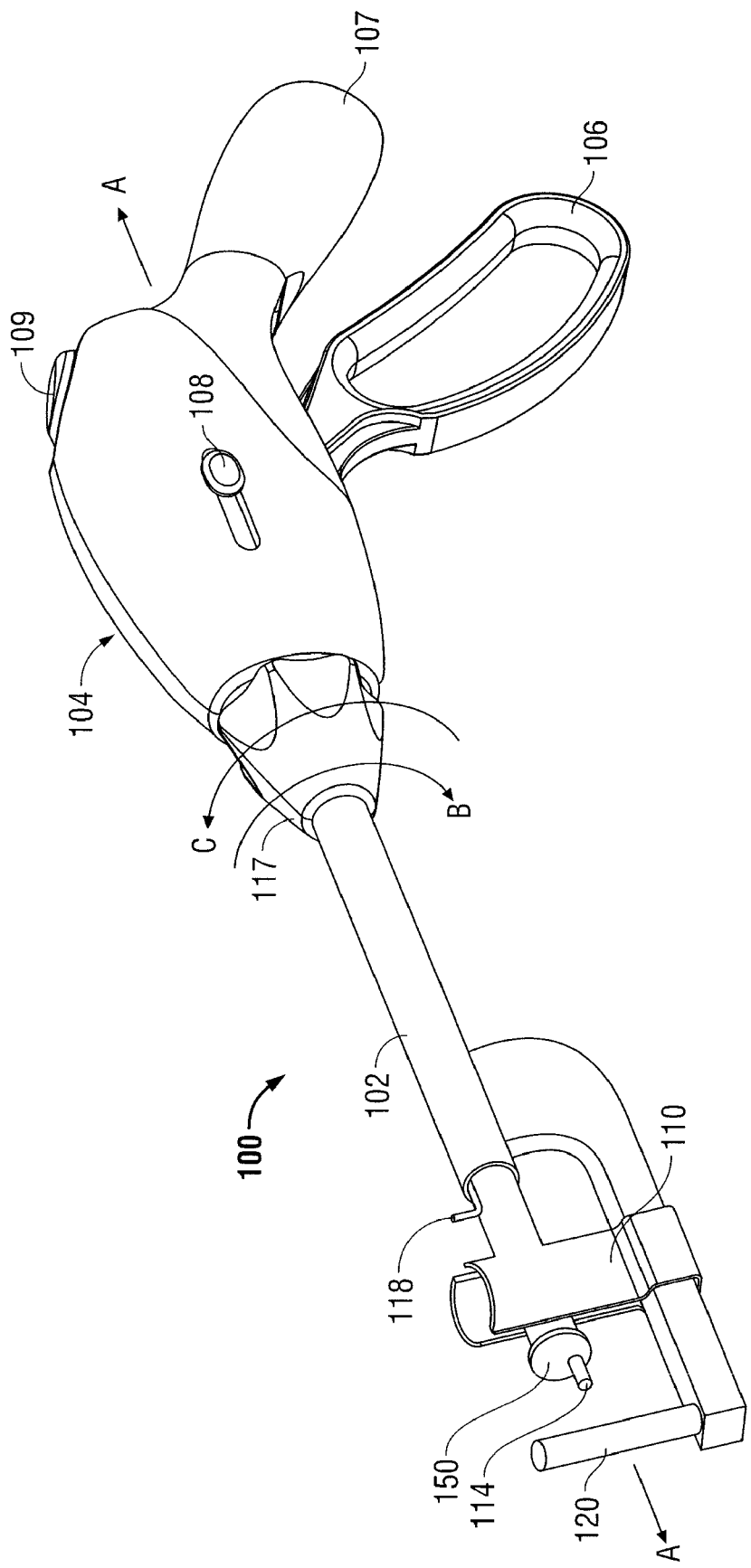
FIG. 1 is a perspective view of a surgical instrument in accordance with the present disclosure where the surgical instrument is shown without a loading unit.

Embodiments of the presently disclosed surgical instrument and loading unit for use therewith, are described in detail with reference to the drawings, wherein like reference numerals designate corresponding elements in each of the several views.

A surgical instrument of the present disclosure is indicated as reference numeral 100 in FIG. 1. A loading unit (or "DLU") 200 for use with surgical instrument 100 is shown in FIGS. 2-5E. While a specific type of a surgical stapling instrument is illustrated in FIG. 1, the present disclosure also relates to other types of surgical stapling instruments and to electrosurgical forceps, and to loading units for use therewith. DLU 200 is attachable to an elongated portion 102 (which defines a longitudinal axis "A-A," as shown in FIGS. 1 and 4) of surgical instrument 100, e.g., to allow surgical instrument 100 to have greater versatility. Elongated portion 102 distally extends from handle assembly 104, which includes movable handle 106 and stationary handle 107. DLU 200 may be configured for a single use, and/or may be configured to be used more than once.

Examples of loading units for use with a surgical stapling instrument are disclosed in commonly-owned U.S. Pat. No. 5,752,644 to Bolanos et al., the entire contents of which are hereby incorporated by reference herein. Further details of an endoscopic surgical stapling instrument are described in detail in commonly-owned U.S. Pat. No. 6,953,139 to Milliman et al., the entire contents of which are hereby incorporated by reference herein. Further details of electrosurgical forceps are described in commonly-owned patent application Ser. No. 10/369,894, filed on Feb. 20, 2003, entitled VESSEL SEALER AND DIVIDER AND METHOD OF MANUFACTURING THE SAME, the entire contents of which are hereby incorporated by reference herein.

Figure 2:
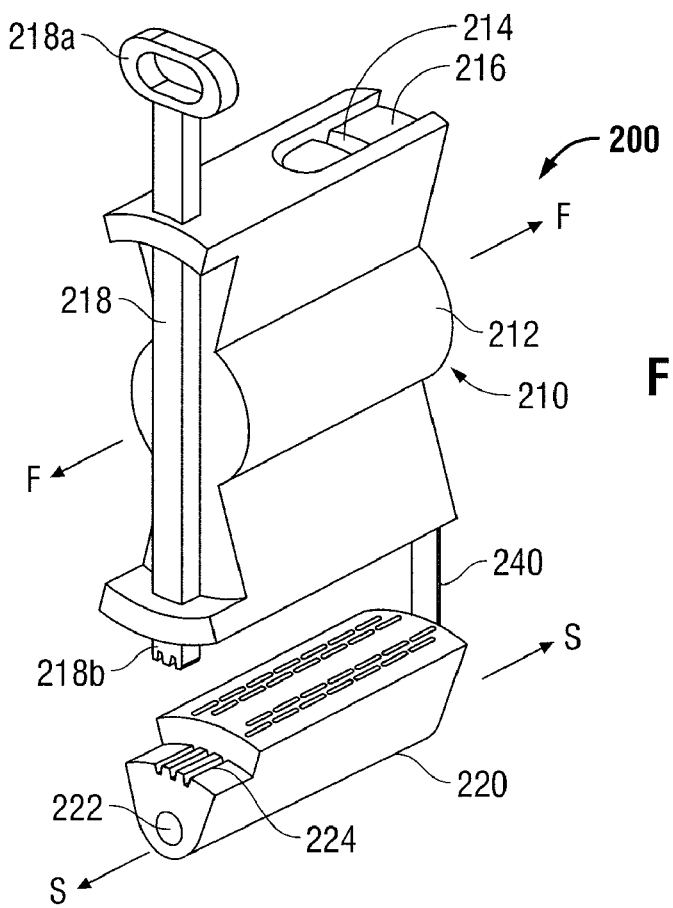
FIG. 2 is a perspective view of a loading unit for use with the surgical instrument of FIG. 1.

Referring now to FIGS. 2-5E, DLU 200 of the present disclosure is shown. DLU 200 includes a first jaw member or cartridge assembly 210 and a second jaw member or anvil assembly 220. In the illustrated embodiments, first jaw member 210 and second jaw member 220 are temporarily connected to one another by a breakable connector 240 (FIG. 2). First jaw member 210 defines a first axis "F-F" (shown in FIGS. 2 and 4) and is configured for releasable engagement with a cartridge housing 110 of surgical instrument 100. Second jaw member 220 defines a second axis "S-S" (shown in FIGS. 2 and 4) and is configured for releasable engagement with an anvil housing 120 of surgical instrument. In the illustrated embodiments, first axis "F-F" and second axis "S-S" are parallel to one another and are each disposed transverse to the longitudinal axis "A-A," but further embodiments include jaw members that are angled with respect to one another and/or to the longitudinal axis. While not explicitly illustrated in the accompanying figures, it is also envisioned that first jaw member 210 and second jaw member 220 are fixed to (i.e., not removable from) surgical instrument 100.

The illustrated embodiments show cartridge assembly 210 having a circular outer portion 212 which is configured to engage a circular inner portion 112 of cartridge housing 110.

With particular reference to FIGS. 5A-5E, the interaction between circular outer portion 212 and circular inner portion 112 helps enable a pivot-type movement between first jaw member 210 and cartridge housing 110. That is, first jaw member 210 is able to pivot (e.g., swivel, rotate, etc.) about axis "F-F" with respect to cartridge housing 110 in the general direction of arrows "W" and "X" in FIG. 3. It is envisioned that cartridge assembly 210 and/or cartridge housing 110 includes other features that help enable the pivot-type movement therebetween. For example, cartridge housing 110 may include a post (not shown) that extends through a bore (not shown) of cartridge assembly 210, or vice versa.

Figure 5D:
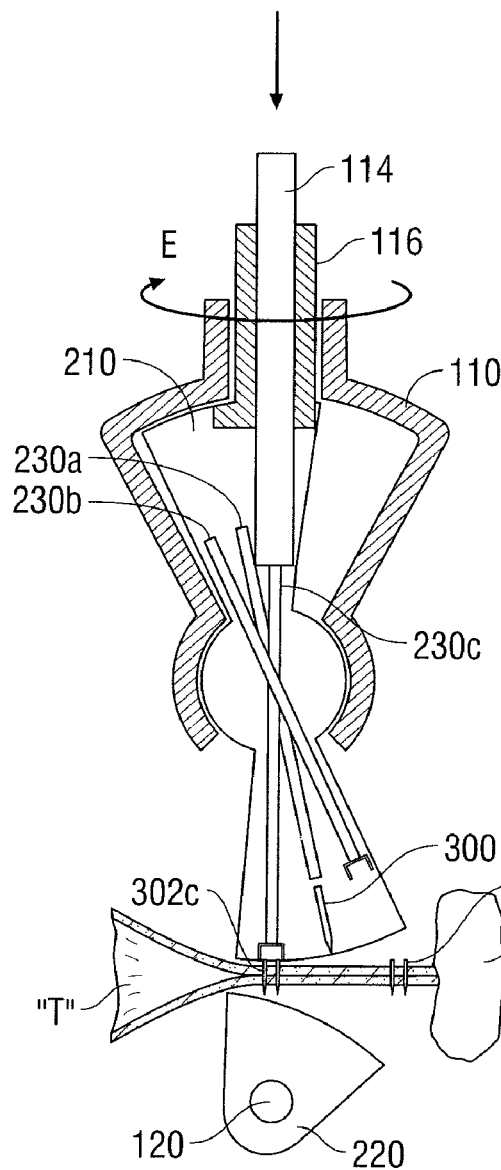

It is envisioned that surgical instrument 100 includes a selector member 116 (e.g., a cam member) disposed in mechanical cooperation with a selector dial 117 (FIG. 1). It is envisioned that rotation of selector dial 117 in the general direction of arrow "B" (FIG. 1) causes selector member 116 to rotate in the general direction of arrow "D" (FIG. 5B). Correspondingly, it is envisioned that rotation of selector dial 117 in the general direction of arrow "C" (FIG. 1) causes selector member 116 to rotate in the general direction of arrow "E" (FIG. 5D). That is, the combination of selector member 116 and selector dial 117 help enable a user to pivot cartridge assembly 210 within cartridge housing 110.

Referring again to FIGS. 2-5E, anvil assembly 220 includes a bore 222 (see FIGS. 2 and 4) extending therethrough. Bore 222 of anvil assembly 220 is configured to mechanical engage anvil housing 120, which is illustrated as a post-like structure. As can be appreciated, the interaction between bore 222 and anvil housing 120 helps enable a pivot-type movement between anvil assembly 220 and anvil housing 120. That is, second jaw member 220 is able to pivot (e.g., swivel, rotate, etc.) about axis "S-S" with respect to anvil housing 120 in the general direction of arrows "Y" and "Z" in FIG. 3. It is envisioned that anvil assembly 220 and/or anvil housing 120 includes other features that help enable the pivot-type movement therebetween. For example, anvil housing 110 may include a circular inner portion (not shown) that mechanically engages a circular outer portion (not shown) of anvil assembly 220, or vice versa.

With particular reference to FIGS. 2 and 4, cartridge assembly 210 includes a first access portion 214 and a second access portion 216. First access portion 214 is configured to accept translation of a firing rod 114 therethrough. Second access portion 216 is configured to allow at least a portion of selector member 116 to pass therethrough. It is envisioned that firing rod 114 is translatable through a portion of selector member 116.

In the embodiments illustrated in FIGS. 2 and 4, cartridge assembly 210 also includes a tissue stop member 218. A proximal portion 218a of tissue stop member 218 is configured to engage a rod 118 of surgical instrument 100. Tissue stop member 218 is movable (via rod 118) with respect to the other parts of cartridge assembly 210 between a first position where a distal portion 218b of tissue stop member 218 is spaced from anvil assembly 220 and a second position where distal portion 218b of tissue stop member 218 engages a portion 224 of anvil assembly 220. More particularly, distal portion 218b of tissue stop member 218 is configured as a portion of a gear and is engagable with portion 224 of anvil assembly 220, which is configured as a corresponding portion of a gear. Specifically, as cartridge assembly 210 and anvil assembly 220 pivot (e.g., in the directions of arrow "W" and arrow "Y," respectively), the portions of the gear rotate therewith. Additionally, portions of the gear may help temporarily maintain the alignment of cartridge assembly 210 and anvil assembly 220 with respect to each other in response to firing staples from cartridge assembly 210, for instance.

Figure 3:
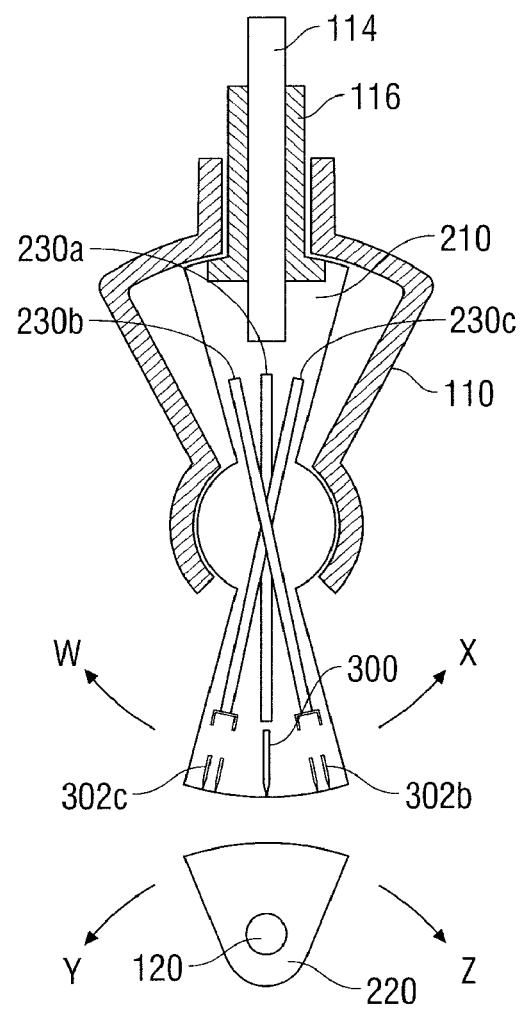
FIG. 3 is a transverse cross-sectional view of the loading unit of FIG. 2.
Figure 4:
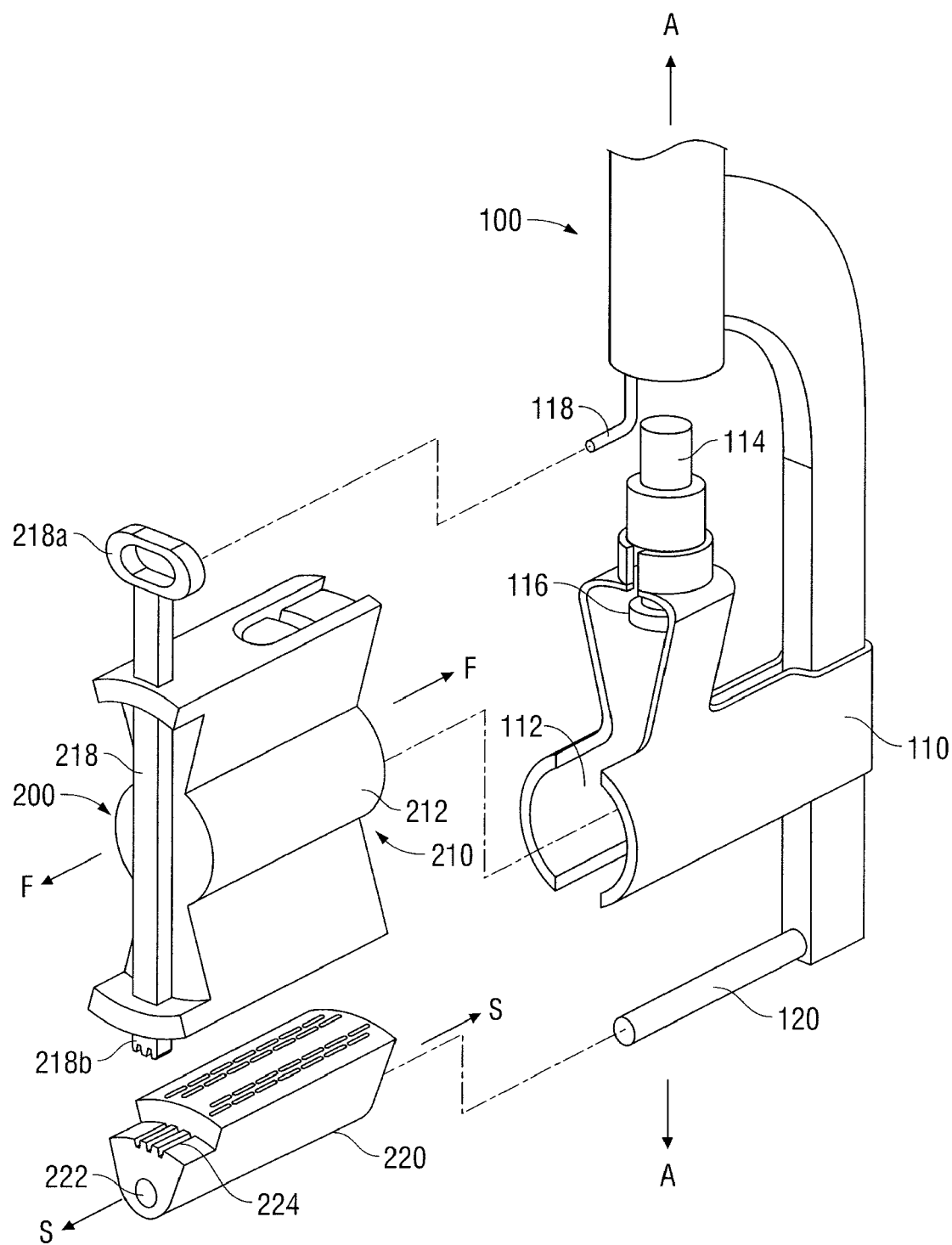
FIG. 4 is an assembly view of the loading unit of FIGS. 2 and 3 and a portion of the surgical instrument of FIG. 1.
Figure 5E:
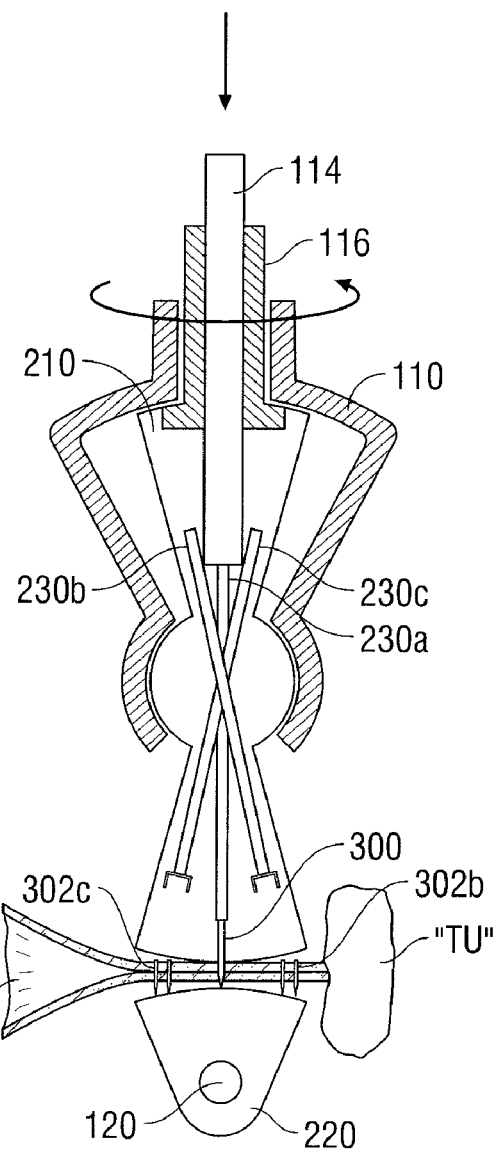

Referring now to FIGS. 3 and 5-5E, the internal components of cartridge assembly 210 are shown. In the illustrated embodiments, cartridge assembly 210 includes three pushers 230a, 230b and 230c (collectively referred to as "pushers 230") therein. It is envisioned that pushers 230 are comb-type pushers that intersect each other. Each pusher 230 is selectively engagable by firing rod 114. The particular pusher 230a, 230b or 230c that is engaged by firing rod 114 is dependent on the orientation of cartridge assembly 210 within cartridge housing 110. That is, when cartridge assembly 210 is in a first position (FIGS. 5A and 5E), firing rod 114 is substantially aligned with pusher 230a; when cartridge assembly 210 is in a second position (FIGS. 5B and 5C), firing rod 114 is substantially aligned with pusher 230b; and when cartridge assembly 210 is in a third position (FIG. 5D), firing rod 114 is substantially aligned with pusher 230c.

Pusher 230a is configured to mechanically engage a knife 300 disposed within cartridge assembly 210, such that actuation of firing rod 114 (in its first position) causes knife 300 to move from a first position (FIG. 5A) where knife 300 is at least partially disposed within cartridge assembly 210 to a second position (FIG. 5E) where at least a portion of knife 300 extends from cartridge assembly 210 to cut tissue. In further embodiments of the present disclosure, the knife is omitted.

Pushers 230b and 230c are each configured to mechanically engage a respective row of fasteners 302b and 302c, which are disposed within cartridge assembly 210. Actuation of firing rod 114 (in its second position) causes pusher 230b to move from a first position (FIG. 5B) where pusher 230b does not engage fasteners 302b, to a second position (FIG. 5C) where pusher 230b engages fasteners 302b to eject fasteners 302b from cartridge assembly 210 towards anvil assembly 220. Actuation of firing rod 114 (in its third position) causes pusher 230c to move from a first position (not explicitly shown) where pusher 230c does not engage fasteners 302c, to a second position (FIG. 5D) where pusher 230c engages fasteners 302c to eject fasteners 302c from cartridge assembly 210 towards anvil assembly 220.

In use, surgical instrument 100 may include DLU 200 mechanically engaged therewith or DLU 200 may be separated therefrom. In the embodiments where DLU 200 is not initially engaged with surgical instrument 100, a user can load cartridge assembly 210 and anvil assembly 220 of DLU 200 into mechanical engagement with surgical instrument 100. Next, a user positions surgical instrument 100 such that target tissue "T" (e.g., tissue to be stapled and cut) is located between jaw members 210, 220. The user may then translate a tissue stop knob 108, which causes distal translation of rod 118 (e.g., in electrical or mechanical cooperation with tissue stop knob 108), which in turn causes tissue stop member 218 to distally translate thus causing distal portion 218b of tissue stop member 218 to engage portion 224 of anvil assembly 220.

To clamp the jaw members 210, 220 with respect to each other (e.g., moving cartridge assembly 210 towards anvil assembly 220), a user at least partially actuates (e.g., fully actuates) movable handle 106 (i.e. moves movable handle 106 towards stationary handle 107). If repositioning of cartridge assembly 210/anvil assembly 220 is desired, a user can actuate a clamp release button 109 to separate cartridge assembly 210 and anvil assembly 220 from each other. It is envisioned that movable handle 106 and firing rod 114 both return to their respective original position after a partial or full stroke of movable handle 106. Thereafter, a user can break connector 240, which temporarily connects/aligns cartridge assembly 210 and anvil assembly 220.

Once jaw members 210, 220 are in their desired location about tissue "T" (FIG. 5A), the user can position selector member 150 via selector knob 117 to align pusher 230b with firing rod 114 (FIG. 5B). Next, if desired, the user can use conventional methods to flush the area adjacent a tumor "TU" to help rid the area of tumor cells. To eject fasteners 302b from cartridge assembly 210 through tissue "T" and towards anvil assembly 220, the user at least partially actuates movable handle 106 which causes distal translation of firing rod 114 into pusher 230b, which forces pusher 230b into engagement with fasteners 302b (FIG. 5C).

Next, with reference to FIG. 5D, the user can position selector member 150 via selector knob 117 to align pusher 230c with firing rod 114. To eject fasteners 302c from cartridge assembly 210, the user at least partially actuates movable handle 106 which causes distal translation of firing rod 114 into pusher 230c, which forces pusher 230c into engagement with fasteners 302c.

After both rows of fasteners 302b, 302c have been fired from cartridge assembly 210, the user can use selector knob 117 to position selector member 150 such that knife 300 is aligned with firing rod 114. To cut tissue, the user at least partially actuates movable handle 106 which causes distal translation of firing rod 114 into pusher 230a, which forces pusher 230a into engagement with knife 300. Alternatively, the user can use a separate instrument to cut tissue "T."

Next, the user can press clamp release button 109 to separate cartridge assembly 210 and anvil assembly 220 from each other, and thus to unclamp tissue "T." Finally, tissue stop knob 108 can be proximally translated to disengage tissue stop member 218 from anvil assembly 220. As can be appreciated, the disclosed method results in the sealing (and separation) of both ends of tissue (e.g., an organ).

It is envisioned that the performing of the various functions of the present disclosure can be accomplished by various suitable methods and are not intended to be limited by the above description. For example, at least one of clamping tissue "T," pivoting cartridge assembly 210, actuating firing rod 114 and cutting tissue "T" can be accomplished via a separate handle or other actuating device (not shown). Additional handles and/or other types of handles can also be used, such as, for example, motor-driven, hydraulic, ratcheting, etc.

It is envisioned that the use of surgical instrument 100 and/or DLU 200 of the present disclosure may help facilitate access to lower pelvis regions, e.g., during lower anterior resection ("LAR").

In further embodiments of the present disclosure, the cartridge assembly houses a first row of surgical fasteners of a first type, and a second row of surgical fasteners of a second type. The user of the surgical instrument may choose to deploy either row of surgical fasteners, or both rows of surgical fasteners, according to the user's judgment. Fastener types include staples of various materials such as surgical steel, other metals, polymers and/or absorbable or resorbable materials, two-part fasteners of various materials, or fasteners of various sizes. For example, the first row of fasteners can comprise staples having leg lengths of a first size, and the second row of fasteners can comprise staples having leg lengths of a second size.

The selector member 150 may be directly actuated by hand or a button or other handle member can be provided on the handle assembly 104 for moving the selector member 150 remotely. The button can be connected to selector member 150 by linkages, cams, gears, or other known mechanisms.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

What is claimed is:

1. A surgical instrument for surgically joining tissue, the surgical instrument comprising:
   a handle assembly;
   an elongated portion extending distally from the handle assembly and defining a longitudinal axis; and
   an end effector disposed adjacent a distal portion of the elongated portion, the end effector including:
      a first jaw member defining a first axis, the first axis being transverse to the longitudinal axis, the first jaw member being pivotable about the first axis; and
      a second jaw member defining a second axis, the second jaw member being pivotable about the second axis, the first and second axes spaced apart along the longitudinal axis; wherein the first jaw member includes a cartridge assembly and the second jaw member includes an anvil assembly, the cartridge assembly including two rows of staples therein and each row of staples is individually actuatable;
      wherein at least one of the first jaw member and the second jaw member is movable with respect to the other between a spaced-apart position and an approximated position.

2. The surgical instrument of claim 1, wherein the second axis is parallel to the first axis.

3. A surgical instrument for surgically joining tissue, the surgical instrument comprising:
   a handle assembly;
   an elongated portion extending distally from the handle assembly and defining a longitudinal axis; and
   an end effector disposed adjacent a distal portion of the elongated portion, the end effector including:
      a first jaw member defining a first axis, the first axis being transverse to the longitudinal axis, the first jaw member being pivotable about the first axis; and
      a second jaw member defining a second axis, the second jaw member being pivotable about the second axis, the first and second axes spaced apart along the longitudinal axis, wherein the second axis is parallel to the first axis;
      wherein at least one of the first jaw member and the second jaw member is movable with respect to the other between a spaced-apart position and an approximated position, the second jaw member being configured to pivot about the second axis in response to pivoting of the first jaw member about the first axis.

4. The surgical instrument of claim 2, wherein the second jaw member is configured to pivot in an opposite direction as the first jaw member.

5. The surgical instrument of claim 1, wherein the cartridge assembly includes a knife disposed at least partially therein and wherein each of the knife and the two rows of staples is individually actuatable.

6. The surgical instrument of claim 5, wherein the cartridge assembly includes three angularly offset pushers disposed therein and wherein each of the three pushers is independently moveable with respect to each other.

7. A surgical instrument for surgically joining tissue, the surgical instrument comprising:

a handle assembly;
an elongated portion extending distally from the handle assembly and defining a longitudinal axis; and
an end effector disposed adjacent a distal portion of the elongated portion, the end effector including:
   a first jaw member defining a first axis, the first axis being transverse to the longitudinal axis, the first jaw member being pivotable about the first axis; and
   a second jaw member defining a second axis, the second jaw member being pivotable about the second axis, the first and second axes spaced apart along the longitudinal axis;
   wherein at least one of the first jaw member and the second jaw member is movable with respect to the other between a spaced-apart position and an approximated position; and
   a firing rod disposed in mechanical cooperation with the handle assembly, the firing rod being configured to individually engage at least two angularly offset pushers disposed at least partially within the first jaw member.

8. A surgical instrument for surgically joining tissue, the surgical instrument comprising:
a handle assembly;
an elongated portion extending distally from the handle assembly and defining a longitudinal axis; and
an end effector disposed adjacent a distal portion of the elongated portion, the end effector including:
   a first jaw member defining a first axis extending along the first jaw member, the first jaw member being pivotable about the first axis and including a cartridge assembly, the cartridge assembly having a first row of surgical fasteners of a first type and a second row of surgical fasteners of a second type; and
   a second jaw member including an anvil assembly, the second jaw member defining a second axis extending along the second jaw member, the second jaw member pivotable about the second axis, the second axis being parallel to the first axis, the first and second axes spaced apart along the longitudinal axis;
   wherein at least one of the first jaw member and the second jaw member is movable with respect to the other between a spaced-apart position and an approximated position.

9. The surgical instrument of claim 8, wherein the first type is selected from the group consisting of: a material, a size, staples, and two-part fasteners.

10. The surgical instrument of claim 9, wherein the second type is selected from the group consisting of a metal material, a polymeric material, a staple leg length, and two-part fasteners.

11. The surgical instrument of claim 10, wherein the first type is different from the second type.

12. The surgical instrument of claim 8, wherein the cartridge assembly includes two rows of staples therein and wherein each row of staples is individually actuatable.

13. The surgical instrument of claim 8, wherein the cartridge assembly includes a knife disposed at least partially therein and wherein each of the knife and the two rows of staples is individually actuatable.

14. The surgical instrument of claim 1, wherein the first jaw member is pivotable independent of the second jaw member.

* * * * *